United States Patent
Levesque et al.

(10) Patent No.: US 10,013,842 B2
(45) Date of Patent: Jul. 3, 2018

(54) METHOD AND SYSTEM FOR ARTICLE MANAGEMENT

(71) Applicant: DISTRIBUTRICES MÉDICALES B.H.L. INC., Rimouski (CA)

(72) Inventors: Stephane Levesque, Rimouski (CA); Michel Boucher, Rimouski (CA)

(73) Assignee: DISTRIBUTRICES MÉDICALES B.H.L. INC., Rimouski (CA)

( * ) Notice: Subject to any disclaimer, the term of this patent is extended or adjusted under 35 U.S.C. 154(b) by 267 days.

(21) Appl. No.: 14/093,104

(22) Filed: Nov. 29, 2013

(65) Prior Publication Data

US 2014/0148947 A1    May 29, 2014

Related U.S. Application Data

(60) Provisional application No. 61/731,243, filed on Nov. 29, 2012.

(51) Int. Cl.

| | | |
|---|---|---|
| *G07F 17/00* | (2006.01) | |
| *G06Q 10/08* | (2012.01) | |
| *G07F 9/02* | (2006.01) | |
| *G16H 40/20* | (2018.01) | |

(52) U.S. Cl.
CPC ....... *G07F 17/0092* (2013.01); *G06Q 10/087* (2013.01); *G07F 9/026* (2013.01); *G16H 40/20* (2018.01)

(58) Field of Classification Search
CPC .................................................. G07F 17/0092
USPC .................................................. 700/231–244
See application file for complete search history.

(56) References Cited

U.S. PATENT DOCUMENTS

| | | | | |
|---|---|---|---|---|
| 5,303,214 | A * | 4/1994 | Kulakowski | G11B 17/225 235/385 |
| 5,812,410 | A | 9/1998 | Lion et al. | |
| 5,905,653 | A * | 5/1999 | Higham | G07F 17/0092 312/215 |
| 6,085,888 | A | 7/2000 | Tedesco et al. | |
| 6,151,536 | A * | 11/2000 | Arnold | G07F 17/0092 700/236 |
| 6,204,763 | B1 | 3/2001 | Sone | |
| 6,438,451 | B1 | 8/2002 | Lion | |
| 6,529,801 | B1 | 3/2003 | Rosenblum | |
| 6,829,520 | B1 * | 12/2004 | Green | G01K 3/04 235/385 |
| 6,874,684 | B1 * | 4/2005 | Denenberg | G07F 17/0092 235/381 |
| 7,734,369 | B2 * | 6/2010 | Godlewski | G06Q 10/087 700/216 |
| 7,887,146 | B1 * | 2/2011 | Louie | A61J 1/16 211/85.15 |

(Continued)

*Primary Examiner* — Timothy R Waggoner
(74) *Attorney, Agent, or Firm* — Gwendoline Bruneau

(57) ABSTRACT

A system and method for article management, the method comprising providing a processor and a terminal connected to the processor, providing a closet comprising at least one module comprising at least one location for an article, each location comprising a presence sensor and a signaling unit, at least one door, a user interface connected to the terminal; wherein the processor controls the door into preventing access to articles stored within the closet in a closed position and allowing access to an article requested through the user interface in an open position if the article is authorized for retrieval by the processor.

9 Claims, 17 Drawing Sheets

(56) References Cited

U.S. PATENT DOCUMENTS

| | | | | |
|---|---|---|---|---|
| 8,033,423 B2* | 10/2011 | Guerra | .................. | G07F 11/165 |
| | | | | 198/463.3 |
| 8,121,725 B2* | 2/2012 | Baker | ..................... | G07F 11/26 |
| | | | | 221/119 |
| 2002/0183882 A1 | 12/2002 | Dearing et al. | | |
| 2003/0216831 A1* | 11/2003 | Hart | ...................... | G06F 19/322 |
| | | | | 700/235 |
| 2004/0068346 A1 | 4/2004 | Boucher | | |
| 2004/0220697 A1* | 11/2004 | Chavez | ............... | G06Q 10/087 |
| | | | | 700/236 |
| 2008/0319581 A1* | 12/2008 | Vahlberg | ............. | G06Q 10/087 |
| | | | | 700/242 |

* cited by examiner

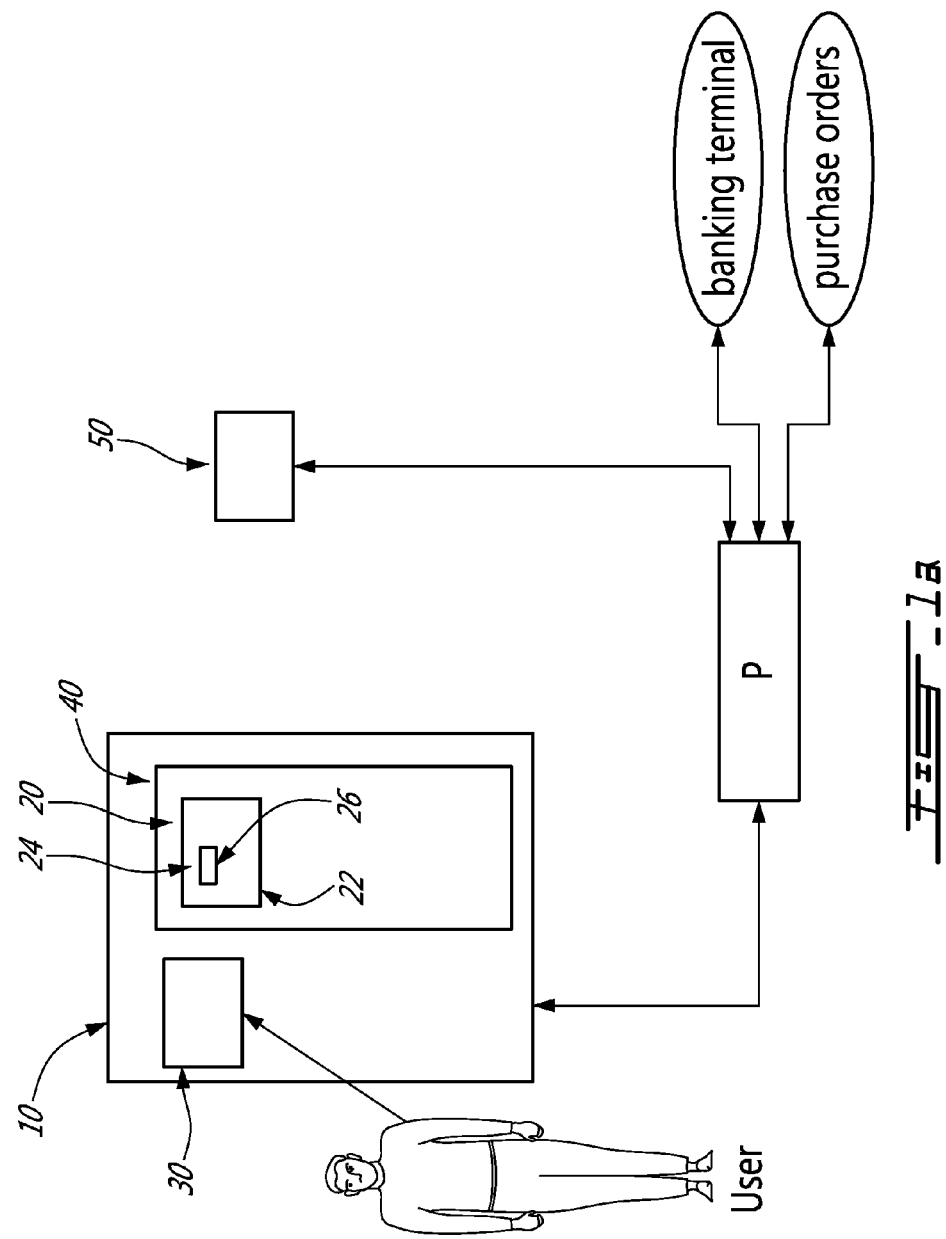

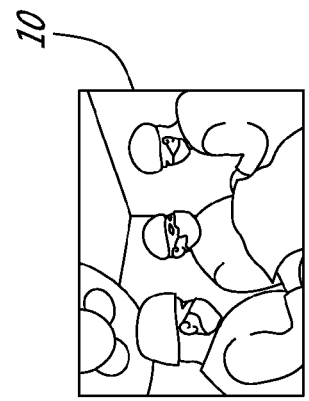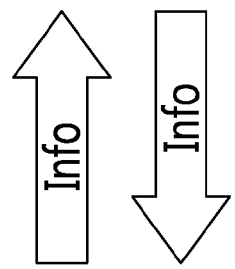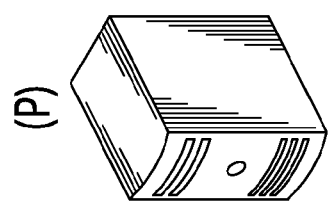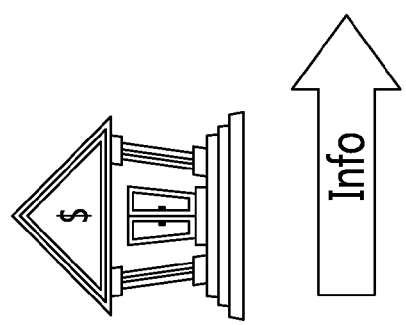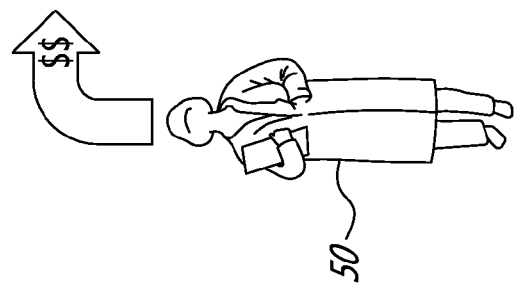
FIG-1b

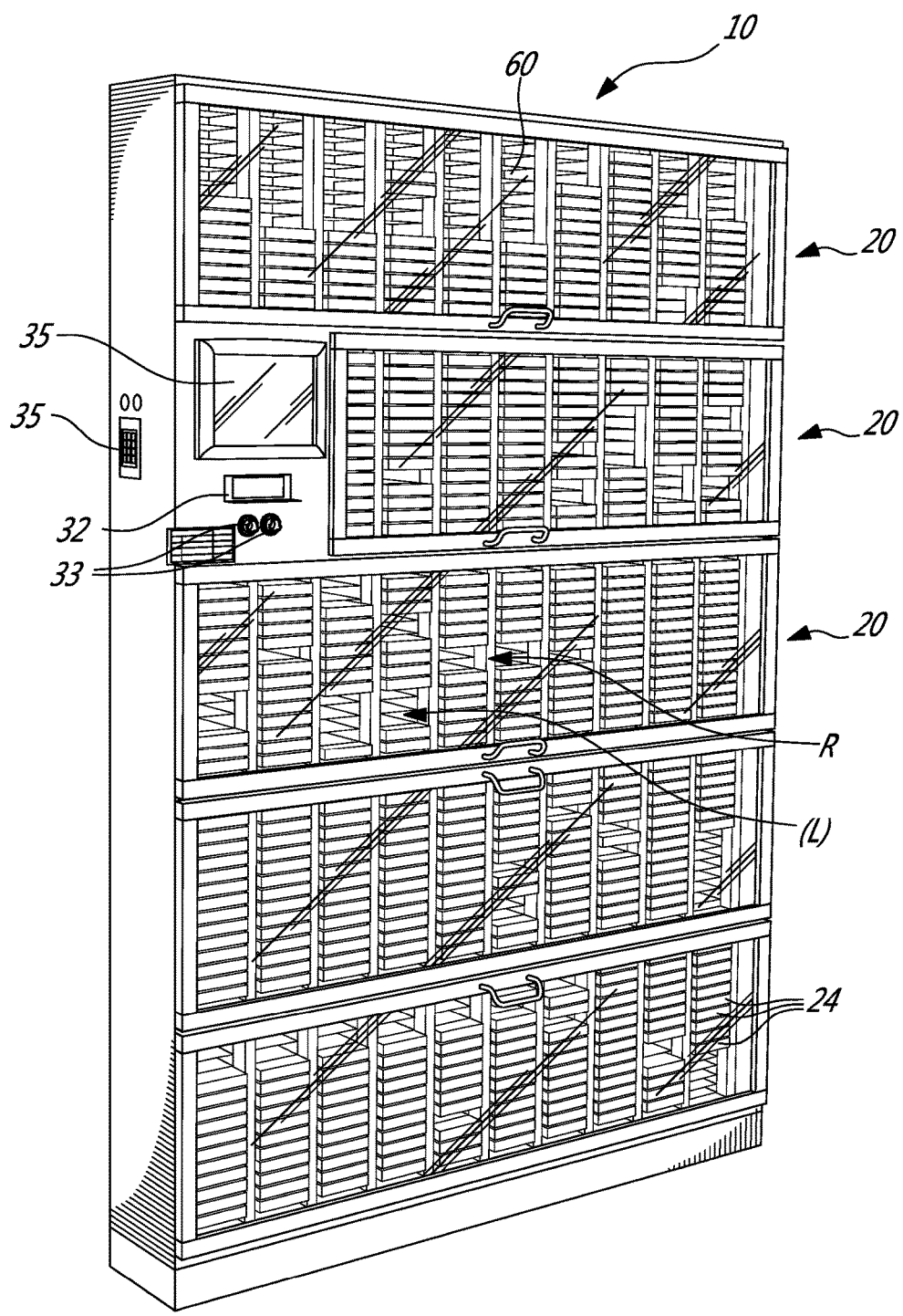

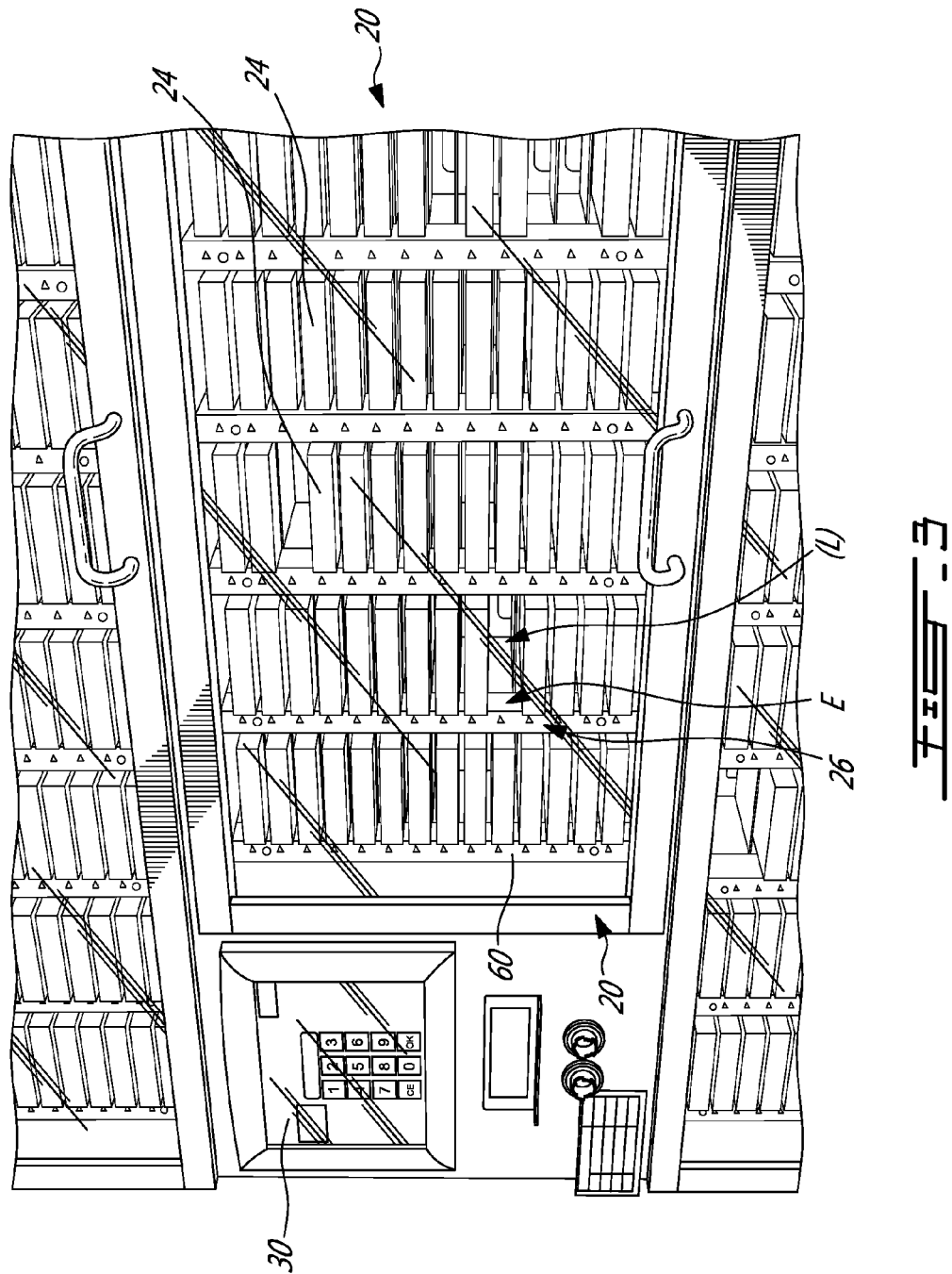

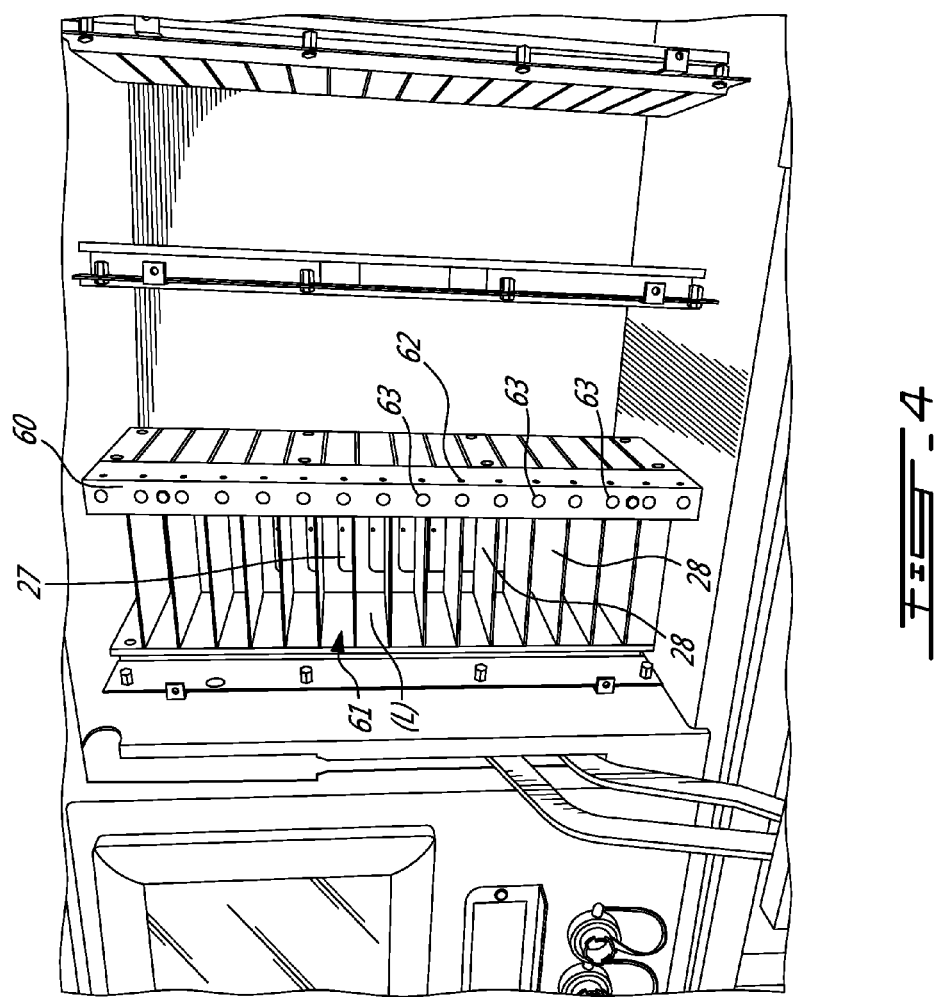

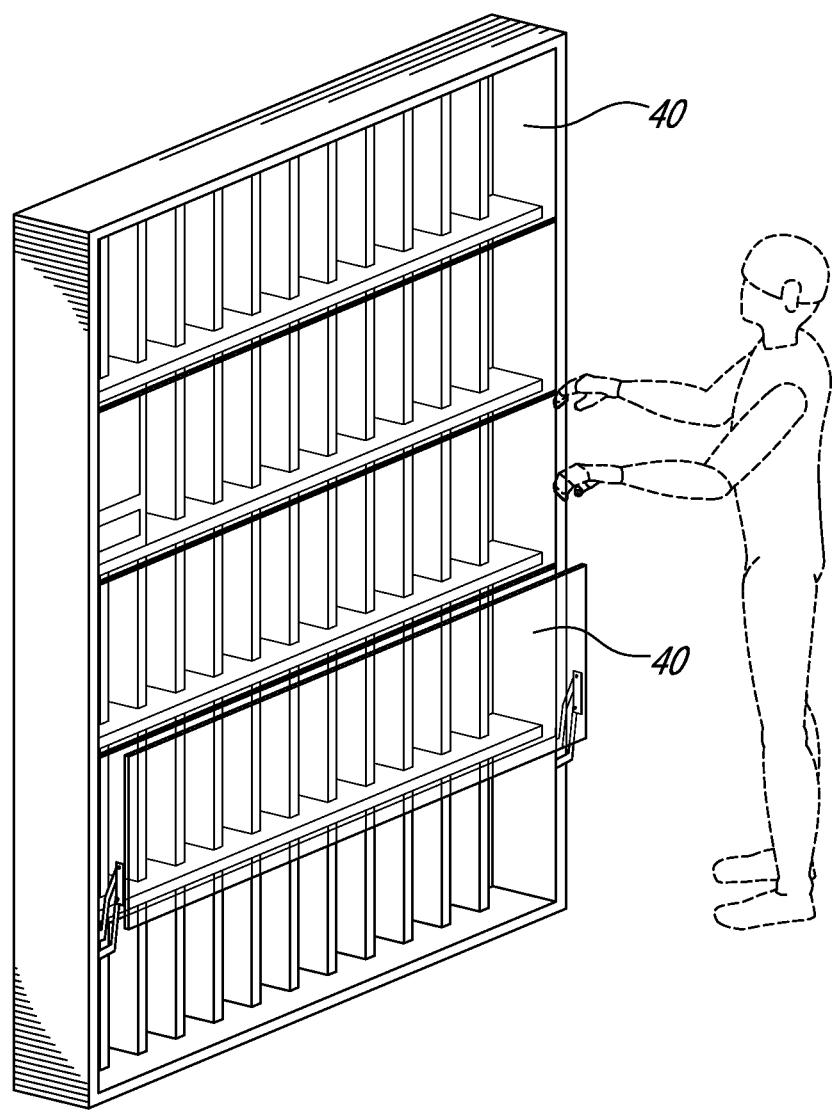

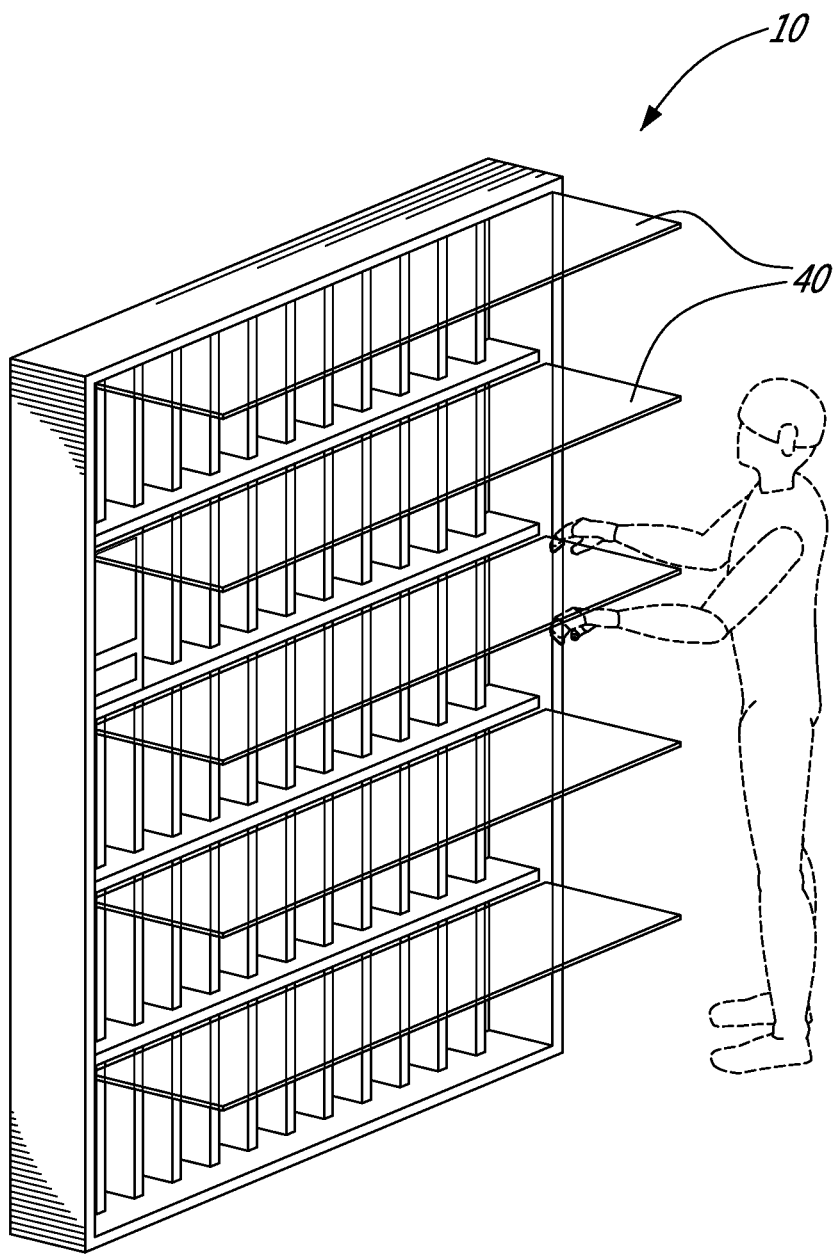

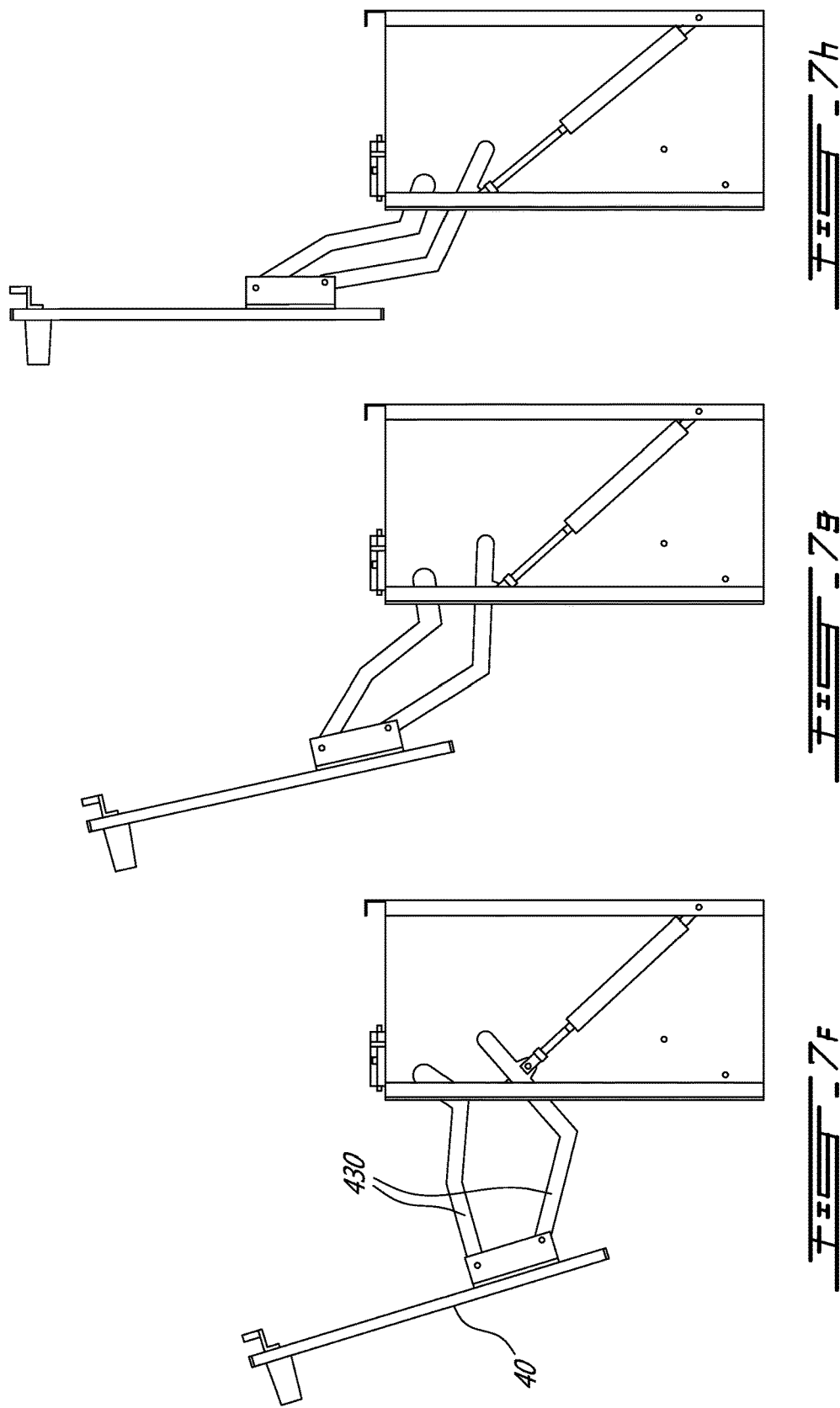

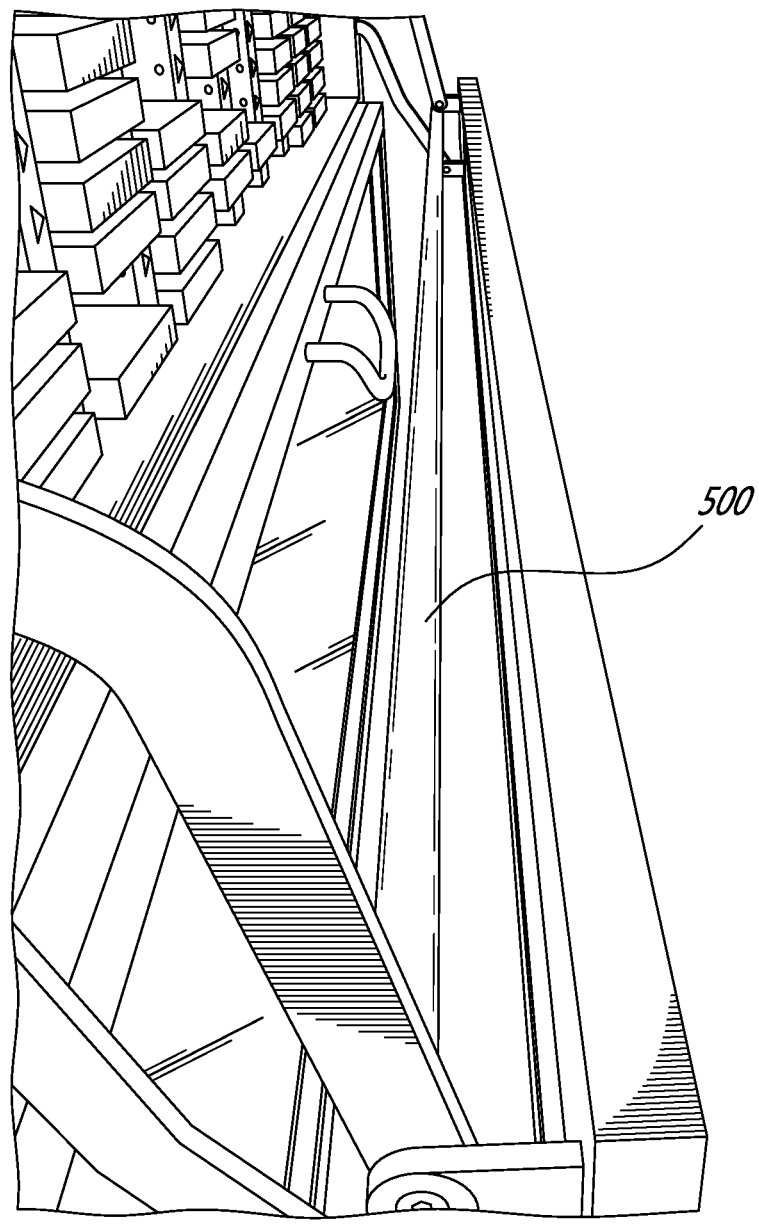

METHOD AND SYSTEM FOR ARTICLE MANAGEMENT

CROSS REFERENCE TO RELATED APPLICATIONS

This application claims benefit of U.S. provisional application Ser. No. 61/731,243, filed on Nov. 29, 2012. All documents above are incorporated herein in their entirety by reference.

FIELD OF THE INVENTION

The present invention relates to article line management. More specifically, the present invention is concerned with a method and system for article line management.

BACKGROUND OF THE INVENTION

Article management may constitute a problem, for example in the medical field. Hospitals and clinics usually have basics systems and methods to keep track of the articles ordered, used or thrown away, and to make sure expired articles are not used on an end-user, i.e. a patient for example. The activities taking place in operating rooms and billing/purchases activities at are typically disconnected, which results in a number of articles being lost or not charged. Inventory, typically manual, is made unreliable since typically the supply cabinets are not secured.

There is a need in the art for a method and a system for article management

SUMMARY OF THE INVENTION

More specifically, in accordance with the present invention, there is provided a closet for article management, the closet comprising at least one module, each module comprising at least one location for an article, each location comprising a presence sensor and a signaling unit; at least one door; a user interface connected to a terminal controlled by a processor; a control board of the closet, communicating with the processor; a control board of the presence sensors, communicating with the processor and with the control board of the closet; wherein the processor controls access to articles stored within the closet in a closed position of the door and allows access to a requested article in an open position of the door if the article is authorised for retrieval.

There is further provided a method for article management, comprising providing a processor and a terminal connected to the processor; providing a closet connected to the processor and the terminal and comprising at least one module, each module comprising at least one location for an article, each location comprising a presence sensor and a signaling unit; at least one door; a user interface connected to the terminal; a control board of the closet, communicating with the processor; a control board of the presence sensors, communicating with the processor and with the control board of the closet; wherein the processor controls the door into preventing access to articles stored within the closet in a closed position and into allowing access to an article requested through the user interface in an open position if the article is authorised for retrieval by the processor.

There is further provided a method for article management, comprising: entering articles identified by a serial number in a closet, each article being positioned in a location within the closet, each location comprising a presence sensor and a signaling unit, each entered article being listed in a database comprising the article's serial number and expiration date and the specific location it is placed within the closet and the status of the associated presence sensor; closing a door of the closet; and, upon a request for an article, by a user through a user interface of the closet, unlocking the door, activating a signaling unit into signaling a location within the closet housing the requested article having a nearest expiration date, allowing the withdrawal of the requested article from the signaled location only, closing the door once the requested article has been retrieved from the location, updating an inventory of the closet, updating a file associated with an end user of the article and generating a purchase order for replacing the article that has been retrieved from the closet; and upon a request, by a user through a user interface of the closet, for replenishing of the closet, activating a scan of all articles already within the closet, locating any expired article, controlling unlocking of the door, and: i) in case an expired article is detected, prompting a user to withdraw the detected expired article from the closet and, only when the detected expired article is withdrawn from the closet, controlling a signaling unit into pointing out to a specific location within the closet in which a new incoming article is to be placed, the presence sensor of the specific location returning a presence signal once the new incoming article is placed in the specific location; ii) in absence of a detected expired article, controlling a signaling unit into pointing out to a specific location within the closet in which a new incoming article is to be placed, the presence sensor of the specific location returning a presence signal once the new incoming article is placed in the specific location; and updating an inventory of the closet.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 1 show *a*) a diagrammatic view of a system according to an embodiment of an aspect of the present invention, *b*) a diagrammatic view of a method according to an embodiment of an aspect of the present invention;

FIG. 2 shows a closet according to an embodiment of an aspect of the present invention;

FIG. 3 shows a detail of a closet according to an embodiment of an aspect of the present invention;

FIG. 4 shows a detail of a module according to an embodiment of an aspect of the present invention;

FIG. 9 is a detail of a door for a closet according to an embodiment of an aspect of the present invention.

DESCRIPTION OF EMBODIMENTS OF THE INVENTION

Figure 5A:
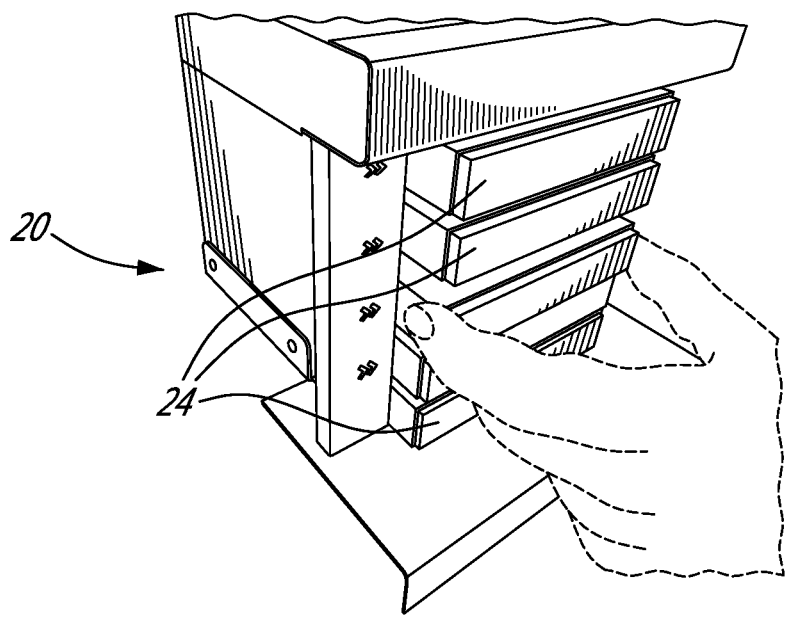
FIGS. 5*a* and 5*b* show details of a module according to an embodiment of an aspect of the present invention.
Figure 5B:
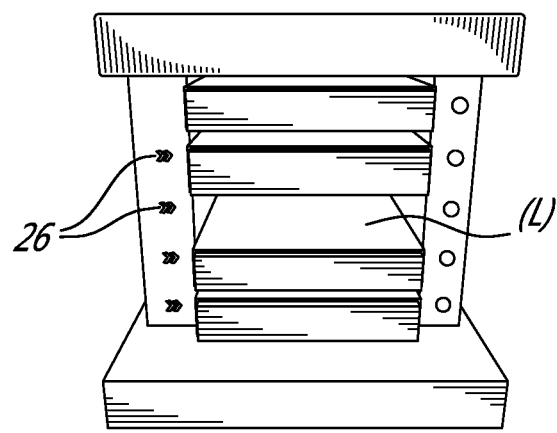

As illustrated in FIG. 1, a system according to an embodiment of an aspect of the present invention comprises a modular closet 10, typically located within an operation room for example, and an administrator terminal 50, typically located out of the operation room, controlled by a processor unit (P).

As illustrated for example in FIG. 2, a closet 10 according to an embodiment of an aspect of the present invention comprises a plurality of modules 20, which can be stacked one on top of the other for example. Each module is provided with position indicators and detents (not shown) on its outside surface so that modules can be stacked in a perfect alignment without torsion which might result in misalignment of the sensor boards discussed hereinbelow.

Each module 20 is associated with presence sensors comprising a IR emitter E and a IR receiver R associated with each location L within the module 20, and each location L comprises a signaling unit such as a light emitting diode (LED) 26 (see FIGS. 2 and 3).

Printed circuits comprising the presence sensors and leds 26 are located on each side of the walls of the module 20, behind a cover 60 (FIG. 4 shows a module without cover 60). The printed circuits may be removed by the front of the module 20 by removing the covers 60 (shown in FIG. 3 for example).

Figure 8A:
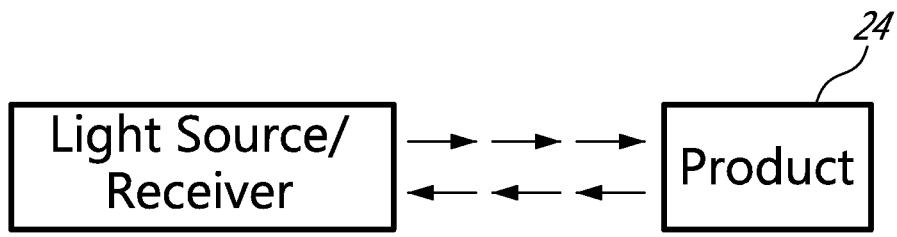
FIGS. 8 *a*), *b*) and *c*) show different methods for detecting presence of a product according to embodiments of an aspect of the present invention.
Figure 8B:
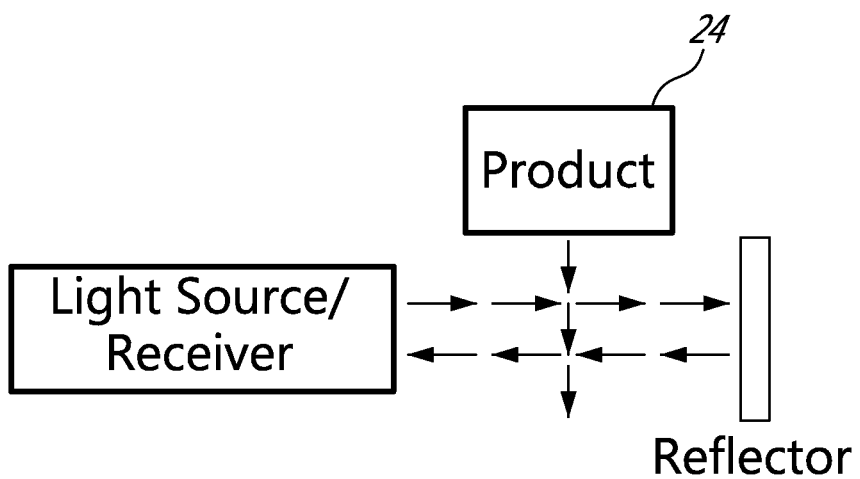
Figure 8C:
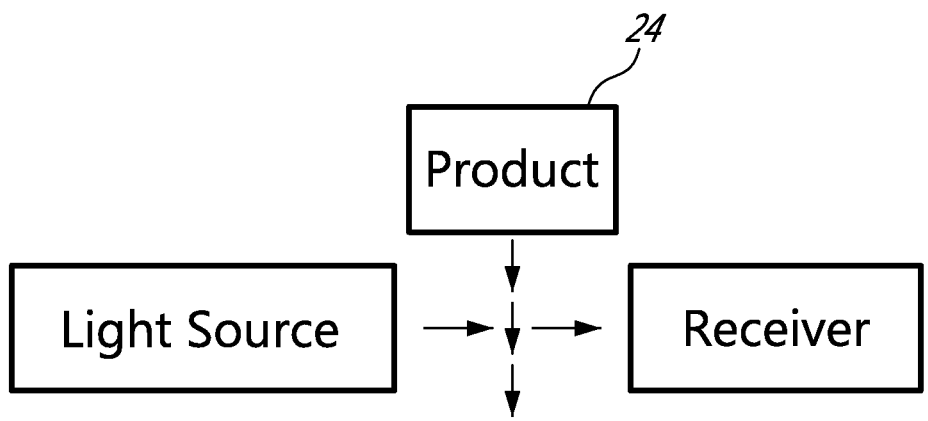

There are different ways to optically detect presence of a product 24 in a location. As shown in FIG. 8, reflection on the product may be used, an ON status of the sensor then corresponding to the presence of a product (FIG. 8a), or reflection using a reflector positioned on the opposite side of the product, an OFF status of the sensor then corresponding to the presence of a product (FIG. 8b), or positioning a light emitter E and a receiver R on each side of the location, an OFF status of the sensor then corresponding to the presence of a product (FIG. 8c). Using an emitter and a receiver are positioned on the same side of the location (FIGS. 8a and 8b) allows minimising the number of required circuit boards: for example, for a stacking of 10 locations, 5 circuit boards would be needed. However, the product within the location may interfere with the sensor sensitivity: in the case of FIG. 8a for example, a product having a weak reflectivity may not be detected; in the case of FIG. 8b, a very reflective product may activate the senor and cause a false result (location empty instead of full).

The case of FIG. 8c allows minimizing false results. This configuration requires more circuit boards. For example, for a stacking of 10 locations, 11 circuit boards are needed. However each circuit board comprises fewer components that circuit boards used for the configurations of FIG. 8a or 8b.

The cover 60 protects the presence sensors control boards, i.e. the boards of the emitters E and the receivers R. As shown in FIG. 4, for each location in a module, the walls of the location comprises apertures 61, 62 allowing passage of rays from the emitter E to the receiver R of the presence sensor associated with the location L, and an aperture 63 for the led of the location L. The cover 60 may be coated with an opaque white sticking film having transparent windows at the positions of the apertures 61, 62, i.e. of the emitters E and the receivers R. An opaque film over the apertures 63 for the leds allows diffusing the lighting of the leds.

Articles 24 may thus be stacked in a module 20, with a separator 28 between each article, as best seen in FIG. 4 for example, so that a given article 24 may be retrieved from the module 20 without disturbing an article located on top or below in the module.

Depending on the format of the articles, separators 28 may be omitted, and then a number of light emitting diode (LED) 26 are not used since the resulting location need only one signaling emitting diode (LED) 26.

Each separator 28 is typically a steel plate having an upward fold 27 at the back thereof, to which the article abuts. Separators of different depths, i.e. with a back fold at different distances from the front of the separators, may be used depending on the size of the articles, so that all articles, when stored in the closet 10, have their front facing on a same line at the front of the module.

A closet 10 may contain a plurality of article lines. Each article line may be contained within a dedicated module of the closet for example.

The closet 10 also comprises a user interface 30 of a user terminal, such as a touch screen, a bar code reader 32, USB ports 33, and a mother board. The mother board of a closet comprises as many ports as the number of modules in the closet. For example, for a module comprising 6 modules, each module comprising between 1 and 16 columns of 16 locations each for example, the mother board comprises 6 ports. The mother board allows locally storing all data; product serial number, product number, product expiration date, location of the product within the closet, date and hour of storage of the product within the closet.

The closet 10 may further comprise a keyboard 35 allowing entering different codes, such as a code for unlocking all doors of the closet 10 in case of power failure, a code for opening a side panel of the closet 10 and gain access to the user terminal housed herein, and a code for resetting the user terminal housed herein for example (see FIG. 2).

The LED 26 signals a location of an article 24 to be retrieved, according to a request for an article from an end user's file, such as a patient's file, to the processor, as input by the user and the durable life date of corresponding articles present in the closet 10 as will be described hereinbelow. The LED 26 may have several colors, to signal articles corresponding to the request with different characteristics, such as: corresponding article with an overdue expiration date, corresponding article before its expiration date etc.

When a given article 24 is retrieved from a module 20, the associated movement sensor at the location of the article within the module 20 sends a signal to the processor. When an article 24 needs to be returned to the closet 10 in case of an error or defects, a LED emitter 26 also lights up to signal which position within the closet the returning article must be put in. Positions in a module may be provided with a weight sensor so as to discriminate between returned articles, for example between an empty package and a package containing an article returned within the casing, which weighs more than an empty package.

Moreover, access to a location in the module may be blocked once a product is retrieved therefrom, thereby preventing unauthorized return of a product in the closet. For example, each location within the closet may be provided with push buttons on each lateral wall of the location, receding within the walls for insertion or withdrawal of a product within or from the location. Once a product is withdrawn from a location, the corresponding push buttons may be blocked in their protruding position, thereby preventing insertion of a product in the just freed location. Similarly, when a product becomes expired, the corresponding push buttons may be operated to protrude from the walls of the corresponding location to lock the identified expired product into position, preventing its retrieval from the location. The push buttons will then be allowed to let go of the expired product only when a user will effectively be prompted to withdraw this product identified as expired, when the user activates a replenishing option, as described hereinbelow, for example.

Figure 6A:
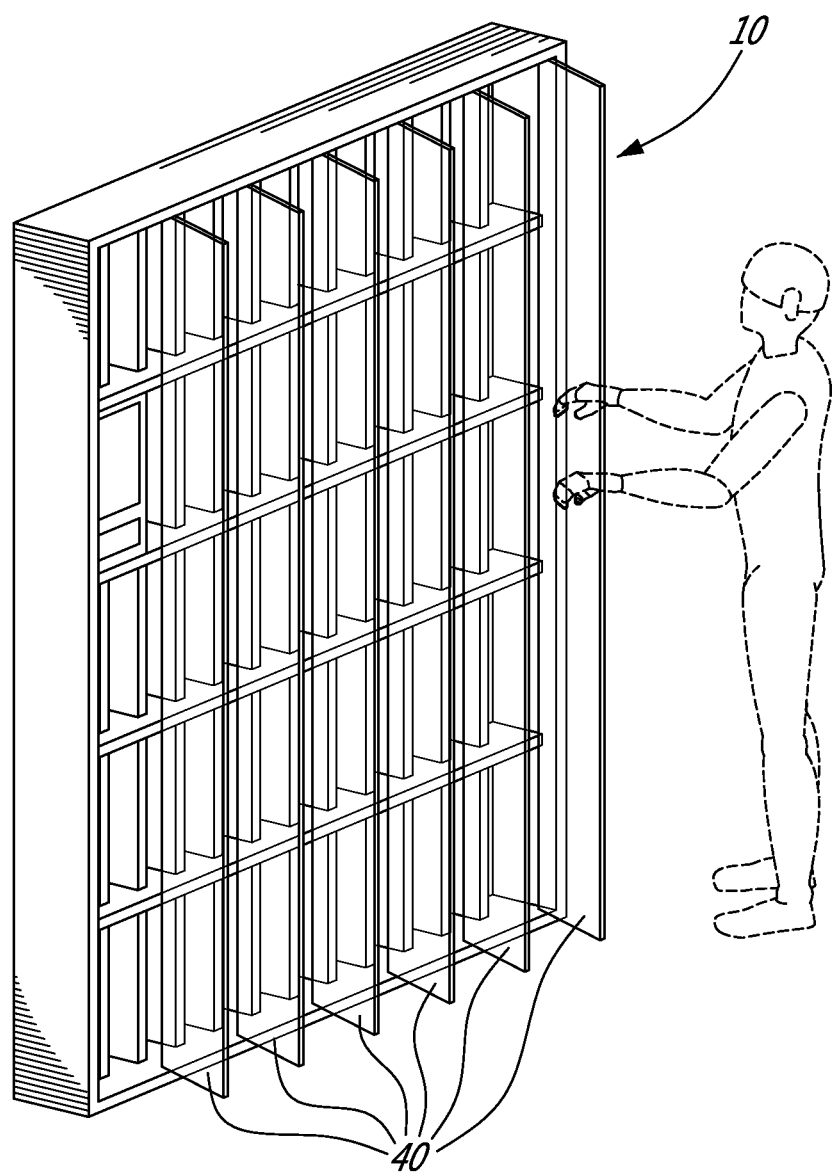
FIG. 6 show *a*) column doors, and *b*), *c*) and *d*) row doors, for a closet according to embodiments of an aspect of the present invention.
Figure 6D:
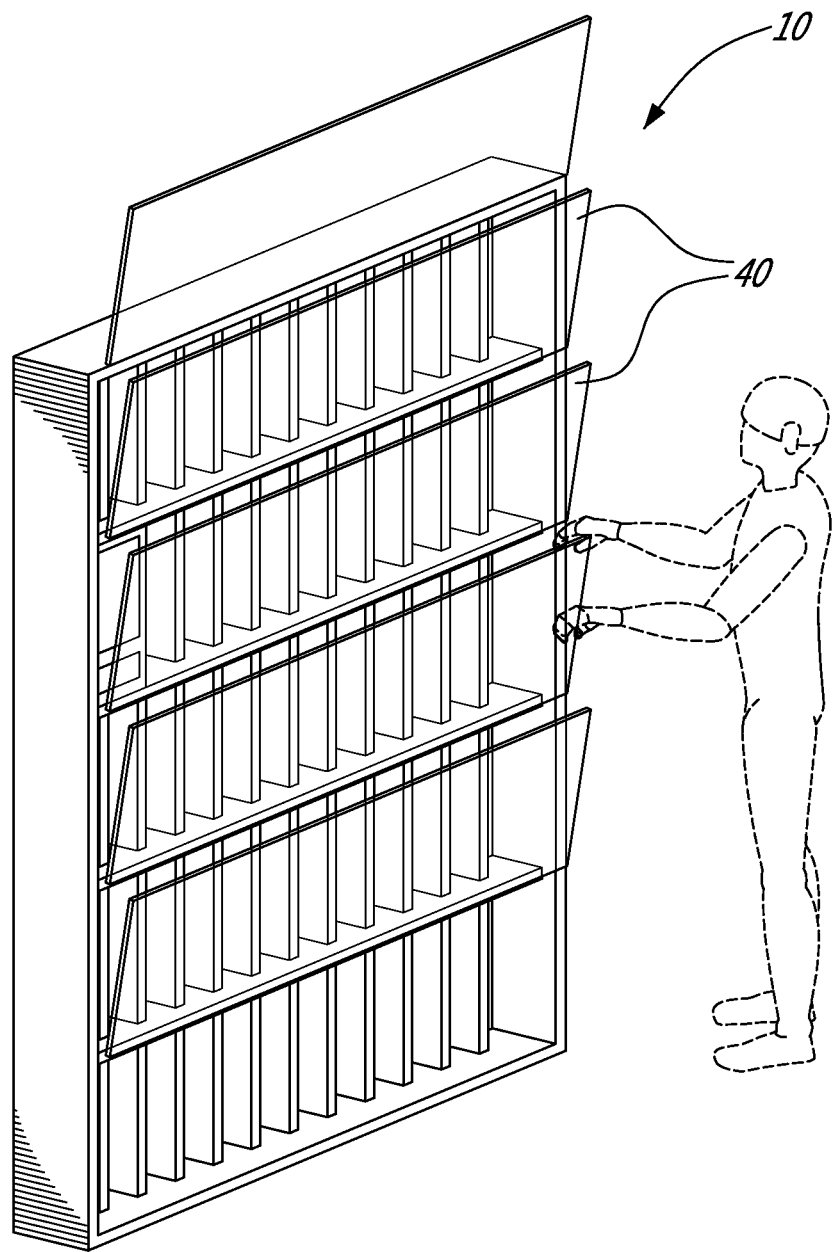
Figure 7A:
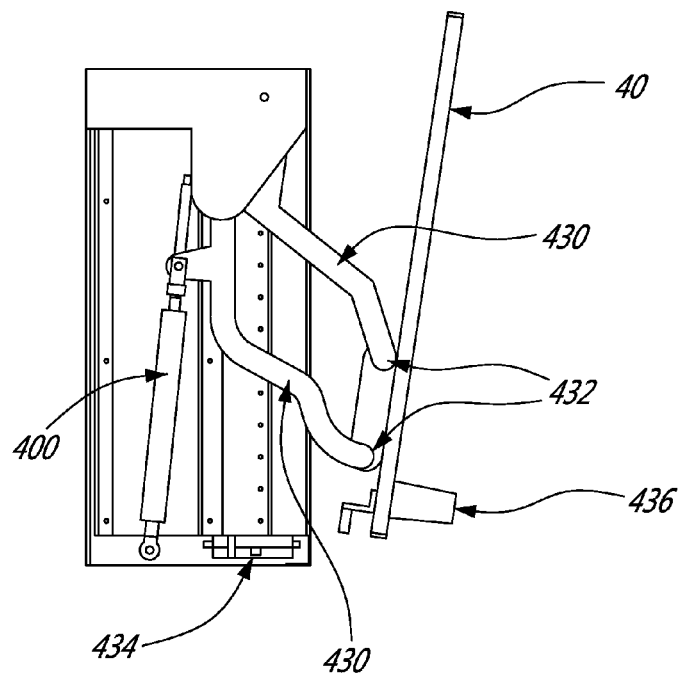
FIGS. 7*a*-7*n* show diagrammatic views of a door for a closet according to embodiments of an aspect of the present invention.
Figure 7B:
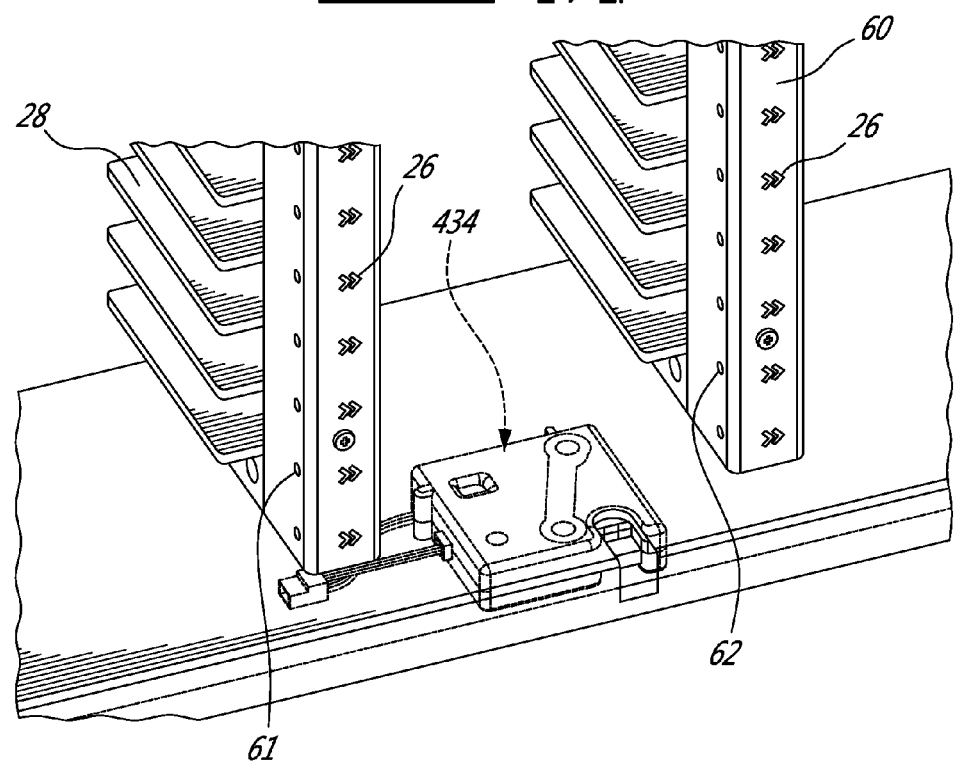
Figure 7E:
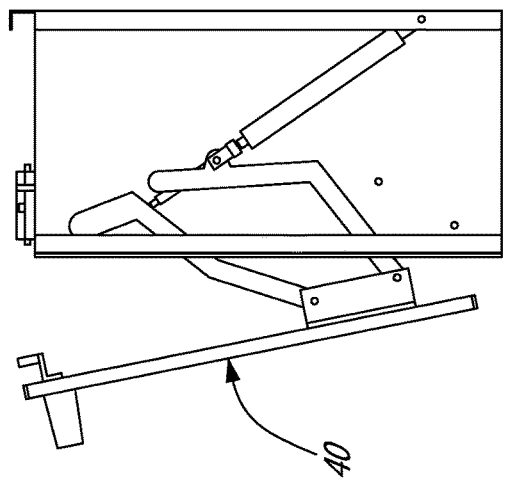
Figure 7D:
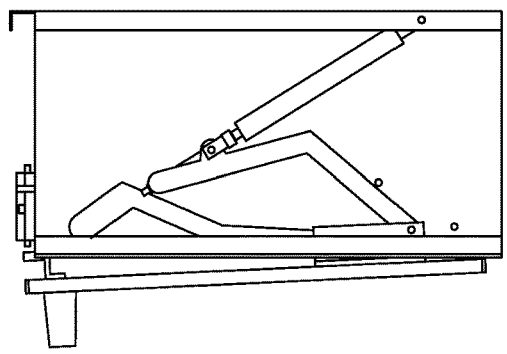
Figure 7C:
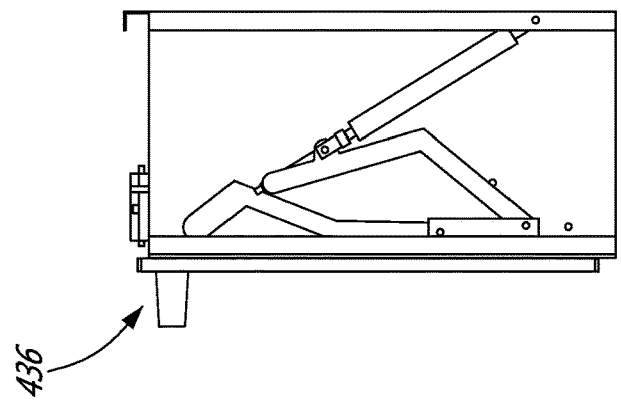
Figure 7K:
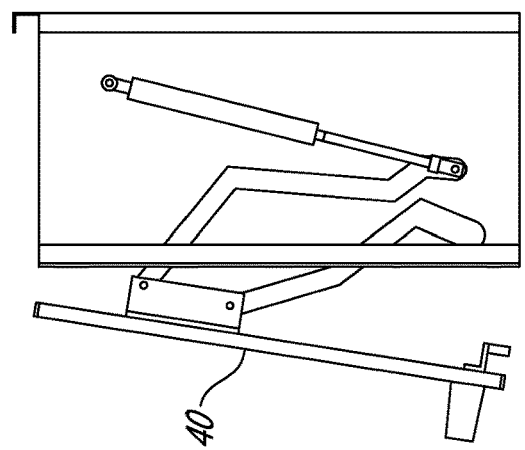
Figure 7J:
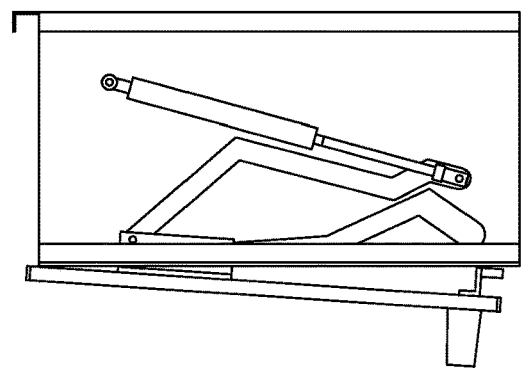
Figure 7I:
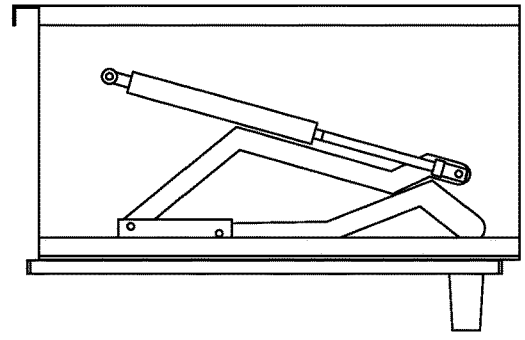
Figure 7N:
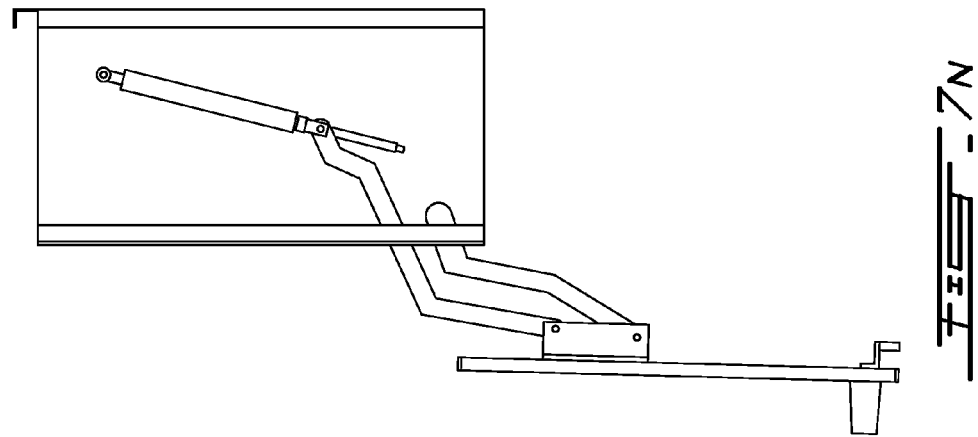
Figure 7M:
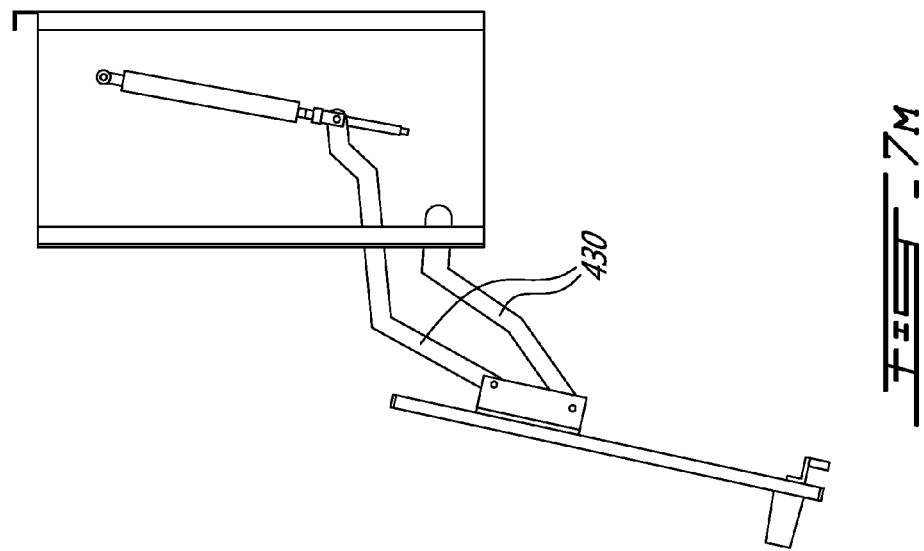
Figure 7L:
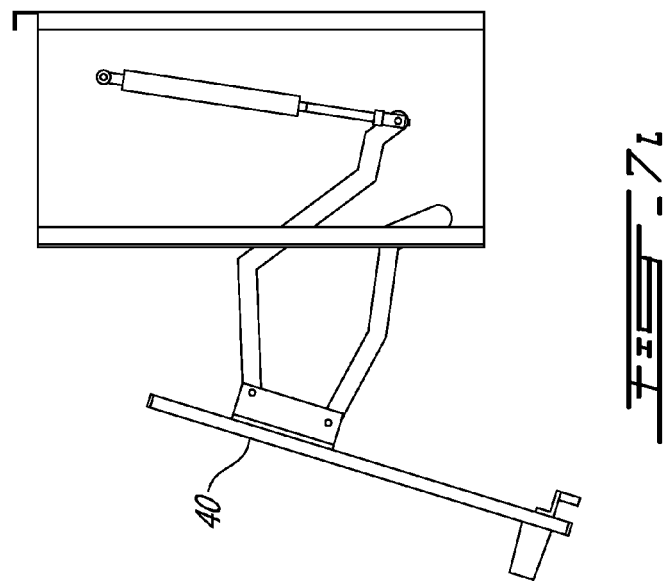

As illustrated in FIG. 6, doors 40 may be provided by columns (see FIG. 6a) or rows (FIG. 6b) for example. FIG. 6a shows vertical doors 40 of the height of the closet 10. FIG. 6b shows horizontal swing-out doors 40 of the width of the closet 10. Horizontal lift doors (FIG. 6c-6d) of the width of the closet 10 may also be used. Vertical doors (FIG. 6a) and horizontal swing-out doors (FIGS. 6b and 7) allow maximizing space within the closet since they only need hinges. On the other hand, horizontal lift doors (FIGS. 6c-6d) may allow minimizing encroachment on the user's space, i.e. in front of the closet 10. Each door is provided with a lock, controlled by the processor as will be described hereinbelow.

FIG. 7 show details of a swing out horizontal door, which can be opened downwards or upwards, by inverting the position of arms 430 supporting the door 40. The door opening system illustrated in FIG. 7 is of the steerable, out-of-way type. Gas cylinders 400 may be used to ease opening of the door 40 supported by arms 430 at pivots 432, and to maintain the door 420 in its open position. The pivots 432 are positioned on the inner surface of the door 40 so that the gas cylinder 400 maintains the door 40 in its closed position when the closing action is over. A latch assembly 434 is positioned at the center of the bottom wall of each module. A latch 434, such as latch Southco R4-EM™, comprising a sensor notifying when the door 40 is in its closed position, may be used.

As shown in FIG. 9, a rod 500 running along the length of the door panel may be added to prevent torsion of the door panel.

The case of a door 40 pivoting open upwards is illustrated for example in FIGS. 7c to 7h. FIGS. 7i to 7n illustrate the case of a door 40 pivoting open downwards, the arms 430 being upside down compared to the latter case.

A module 20 may be preassembled with its door(s), its presence sensors boards and leds, and its connectors, and then, once installed in an operating room for example, the separators 28 and the covers 60 may be positioned.

For a quick detection, i.e. in less than about 1 second, of the presence of a number of articles 24, for example several hundreds, even several thousands of articles, in a closet 10, SPI printed circuits for the presence sensors boards are selected and modified so as to overcome voltage drop due to the length of wiring, connections and printed circuits, during high demand of current and during reading of the locations L in the modules. More precisely, a regulator is added on the sensor boards, thereby allowing using a higher voltage (for example 9V) from the control board and regulating the voltage to 5V for each sensor board. The presence sensors boards are selected to operate at 5 V, so as to have enough power at the leds while minimising unwanted noise in communications The closet 10, or at least selected modules 20 thereof, may be maintained at ambient temperature, or refrigerated or maintained at freezing temperatures, depending of specific requirements of the stored products. A temperature control system may include temperature and humidity sensors, and compressors.

As illustrated in FIG. 1b, the processor is adapted to run a program for managing operation of the system, including retrieval of articles 24 from the closet 10, typically located in an operating room, replenishing of the closet 10 and payment of the articles 24 used from the closet 10.

The program communicates with the mother board of the closet and the control boards of the presence sensors so as to send different commands including: CPU reset, inventory, Debug, Status, Open, Close as will be described hereinbelow. In return, the program allows treating the signals from the mother board and the control boards of the presence sensors. Each change of state of a presence sensor triggers a signal to the program. The mother board also stores a copy of the different states and signals as a backup in case of a failure of the program.

The program allows communication in real time between the closet 10, the administrator terminal 50 and the processor (P) via the Web, so as to control opening of a door 40 of the closet 10, transmission of a new transaction, a replenishing action, an inventory, email alerts on case of quantities below a predetermined threshold, addition or modification of a user, such as a nurse or a doctor, of the closet, addition or modification of an article 24 in the closet 10 (description, price and critical quantity in store in the closet 10), addition of a patient file, listing of article lines, addition of a article, withdrawal or replacement of an article. The information is always updated in real time to that on the program.

The program is connected to a data base containing a list of articles, a list of patient files, an inventory of the modules, a user list, an article line list, an article type list, a list of door locks. These databases are also on the boards of the presence sensors for back up. At any time, the databases attached to the program and of the presence sensor boards are identical. In case of a mismatch, an error signal is delivered by the program.

The program comprises a configuration file allowing setting up the system by setting the number of presence sensor boards, the port of the presence sensor boards, the communication protocol with the presence sensor boards, i.e. USB or RS-232 for example, and selecting options for the program such as payment done, payment to come etc.

The program allows two modes, including an administrator mode and an operating mode, and is adapted for different interfaces. An access code determines which mode is activated.

In the administrator mode, different options are offered: replenishing, locking/unlocking the closet doors, listing of expired articles, data base cleaning, email test so as to check that the internet connection is operational, checking signaled errors, adding a user, etc.

Selecting the replenishing option triggers unlocking of the doors 40, so that upon reading an identification feature of an article 24 to be put in the closet 20, for example its diopters in case of ocular lenses, by reading the bar code provided on the package thereof and containing the serial number of the product, as available on the article, without extra encoding, thereby avoiding risks of tag criss-crossing and errors, with a portable bar code reader or a bar code reader integrated within the closet for example (see 32 FIG. 2), a led 26 lights up at an empty location in a module 20 predetermined by the system to receive the corresponding dioptres, signaling where the article 24 should be placed. Once the article 24 is thus positioned within the closet 10, the associated presence sensor 26 sends a presence signal corresponding to a proper positioning of the article 24. Articles 24 may thus be put within the closet 10 one by one and correspondingly detected by the presence sensors 26. Once the replenishing action is completed, the inventory may be updated, by sending an inventory request signal to each presence sensor. The response signals from the presence sensors are gathered and transferred to the inventory database of the processor and of the presence sensor control board.

In an embodiment of the invention, the replenishing option may be activated only after withdrawal of an expired product from the closet in the event the closet contains one: when a user selects the replenishing option, a scan of all products within the closet may first be performed so as to locate any expired product. If an expired product is detected, then the user is prompted to withdraw the detected product, pointed out to the user by its corresponding led, and only when the identified product (or products) has been withdrawn from the closet, as detected by the presence sensors and/or weight sensors, is the user allowed to go on with the replenishing option. Such mechanism allows avoiding expired products remaining any extent of time within the closet.

Using the code provided on the product package without recurring to any new identification code allows a continuous tracking of the product, from its supply to its input within the closet and its use out of the closet while reducing the risks of incorrect identification. Moreover, in case of a product recall by the manufacturer, the targeted products are thus easily identified and located within the closet. Similarly, expiration date may be safely tracked and monitored.

In the operating mode, when a user such as doctor for example enters his identification number using the user interface 30, the user is asked to enter a patient file identification number. Entry of the patient file identification number may be done manually using a touch screen for example, or by reading an identification card, such as a hospital card, using a HD camera for example, or by magnetic reading identification card. If the patient file identification number entered is part of the list of patient file identification numbers of the system, it means that the article was paid for. Then the user enters the type of article needed, which triggers opening of a door letting access to a corresponding module 20 of the closet 10 and lighting up of a positioning led 26 signaling the requested article 24 within the module 20. If the patient file identification number entered is not found in the list of patient file identification numbers of the system, the user needs to indicate whether the article is paid otherwise than directly by the patient, for example by a Health Insurance Board in case of a medical article, or the article if medically required. Another optional selection may be to indicate a delayed payment by the patient. Thus the use and payment or nonpayment of each article is documented. Then the user enters the type of article needed, which triggers opening of a door to a corresponding module of the closet and lighting up of a positioning led signaling the requested article within the module. The program monitors the expiration date of the articles within the closet and thus always directs to a corresponding article having the nearest expiration date, while always directing to a non-passed expiration date. In case a product within the closet reaches its expiration date, the program automatically withdraws it from the list of available product so that the expired product does not appear on the interface as being available. In case the user, once the doors of the closet are open, tries to withdraw a product after its expiration date, an alarm is triggered. Moreover, the product may be locked into position by lateral push buttons as described hereinabove.

Alternatively, the daily list of planned procedures of the facility or hospital unit for example may be imported from the administrator terminal 50, so that the user only has to select its end user, i.e. patient, from a list appearing on the user interface 30, and then the corresponding article needed from the closet for the specific end user also appears on the user interface 30.

The user can then access the inside of the closet and retrieve the requested article. The user is then prompted to enter an identification number of the retrieved article, for example by reading its bar code and to close the door, or the identification number of the retrieved article is automatically sent to the administrator terminal 50 to update the end user's file and generate an order for replacing the article. The door may close automatically after a predetermined delay of time allowing retrieval of the article. When the presence sensor board detects closing of the closet, it sends a closing signal to the program, which then starts its inventory routine by interrogating each presence sensor.

When a product is retrieved, the patient file associated with the use of the product is correspondingly updated.

When the signals from all presence sensors are received, the list of articles withdrawn from the closet is updated, stored in a sale database and used to update the inventory.

The program allows automatic updates at desired intervals.

The program allows preventing access to given articles within the closet at all times. For example, in case an article was returned within the closet due to a defect, this article is thus prevented from being retrieved by not being signaled by a presence led.

The program thus keeps track of all outputs from, and inputs into, the closet and is able to generate corresponding purchase orders allowing the purchasing department to replenish the closet.

The processor also runs a payment program. The administrator terminal 50, typically located at the cashier of the hospital or in the doctor's office for example, is used by an administrator to ensure keep track of each use of articles used in the operating room. The administrator enters a patient file identification number and a type of article prescribed by a specialist, using again a touch screen for example. Then the administrator selects a mode of payment, i.e. credit, debit or cash, and then the amount is automatically transferred to a banking terminal in case of a credit or debit card for example. Once the transaction is allowed, a receipt is printed and given to the patient. Following each transaction, the file number is forwarded via the web or via modem from the cashier or doctor's terminal 50 to the terminal 30 in the operating room.

Thus, upon entry of the patient file identification number by the nurse or doctor in the terminal 30 located in the operating room as described hereinabove, a window appears either confirming payment of the article in case the patent has previously paid for it, or confirming a subsequent billing corresponding to the cost of the article in case it was not previously paid for, before the doors of the closet are opened to allow retrieving the desired article. The patient file is also updated to indicate the specific product provided to the patient.

There is thus provided a system including a modular closet that can be adjusted to the format and size, as well as to the number, of articles to be distributed, integrates a movement detection mechanism allowing keeping track of the articles and a signaling mechanism directing replacement and retrieval of articles therewithin. The closet can be adapted to meet sterilization norms required in operating rooms.

The present method provides monitoring product use in real time, locating a product at any time, monitoring expiration dates of products, generating orders, based directly on the serial number of the products as provided by the supplier without using other code and allows an efficient tracking of the products, and updating patients' files.

The scope of the claims should not be limited by the embodiments set forth in the examples, but should be given the broadest interpretation consistent with the description as a whole.

What is claimed is:

1. A method for individually and independently continuously tracking articles from a supply thereof with identification features thereof to a use thereof in relation to an end user in absence of intermediate identification input, comprising, for each incoming article, reading the identification features of the incoming article and individually and independently tracking the article continuously from the supply thereof to the use thereof in relation to the end user using the identification features thereof, the method comprising:
   providing a processor and a terminal connected to the processor; and
   providing, in the operating room, a closet comprising: at least one module, each module comprising at least one location, each location comprising an optical presence sensor and a signaling unit; at least one door; a user interface connected to the terminal; a control board of the closet, communicating with the processor; a control board of the presence sensors, communicating with the processor and with the control board of the closet;
   wherein, for replenishing of the closet, a program run by the processor controls unlocking of the door, reading of the identification features of an incoming article, placing the incoming article within an empty location, the presence sensor of the location returning the identification features of the incoming article placed therein to the control board of the presence sensors and to the control board of the closet and the program updating an inventory of the closet with the identification features of the incoming article and the location thereof;
   wherein, for retrieving an article stored with the closet, a program run by the processor controls identification of a user through the user interface of the closet, identification of an article the user requests using identification features of the article the user requests and identification of an end-user of the requested article, and localisation of a location housing an article having the manufacturer identification features and a nearest expiration date within the closet, unlocking of the door, activation of a signaling unit into signaling the localised location, selectively allowing the user to withdraw the corresponding article from the signaled location, closing of the door once the corresponding article has been retrieved from the signaled location, the presence sensor of the signaled location returning an absence signal of the withdrawn article by its identification features to the control board of the presence sensors and to the control board of the closet and the program updating an inventory of the closet with the identification features of the retrieved article and the location thereof; and
   wherein the processor controls the door into preventing access to articles stored within the closet in a closed position and allowing access to an article requested through the user interface in an open position if the article is authorised for retrieval by the processor.

2. The method of claim 1, the program controlling retrieval of articles from the closet, replenishing of the closet, payment of articles used from the closet, and real-time tracking of operation of the closet.

3. The method of claim 1, the program controlling retrieval of articles from the closet, replenishing of the closet, payment of articles used from the closet, and real-time tracking of operation of the closet, the program being connected to a data base containing at least a list of articles, a list of users, a list of end users, a list of the modules, and a list of door locks.

4. The method of claim 1, wherein the program activates a scan of all articles already within the closet, locating any expired article, controlling unlocking of the door, and:
   in case an expired article is detected, the program prompts a user to withdraw the detected expired article and, only when the detected expired article is withdrawn from the closet, controls a signaling unit into pointing out to a specific location within the closet in which a new incoming article is to be placed, the presence sensor of the specific location returning a presence signal once the new incoming article is placed in the specific location, and the program updating an inventory of the closet.

5. The method of claim 1, the program controlling payment of articles retrieved from the closet and generation of replacement articles orders.

6. The method of claim 1, the program controlling insertion of the incoming article in a specific location of the closet, by activating buttons of the specific location into blocking access to the specific location.

7. The method of claim 1, the program monitoring expiration date of articles stored within the closet, the program automatically scanning all locations containing an article in the module and checking an expiration date of the stored articles and activating blocking access to locations detected as containing expired articles.

8. The method of claim 1, the program automatically scanning all locations containing an article in the module and checking an expiration date of the stored articles, activating blocking access to locations detected as containing expired articles, and prompting a user to withdraw the detected expired articles.

9. A method for tracking article management, comprising:
   providing a closet comprising locations, each location comprising an optical presence sensor and a signaling unit;
   providing articles from a supplier, each article having identification features provided by the supplier;
   entering the articles identified by identification features thereof one by one in the closet, each article being positioned in a location within the closet, and transferring, for each article positioned within the closet, a response signal from the presence sensor of the location it is positioned in together with the identification features of the positioned article, to an inventory database, thereby uniquely associating each article with a unique location thereof within the closet by the identification features of the article;
   closing a door of the closet;
   upon a request for an article, by a user using identification features thereof, through a user interface of the closet, for an end user, determining in the inventory database a location within the closet housing the requested article having a nearest expiration date, unlocking the door, activating a signaling unit into signaling the location within the closet housing the requested article having the nearest expiration date, selectively allowing the withdrawal of the requested article from the signaled location, closing the door once the requested article has been retrieved from the location, updating the status of the associated presence sensor, the inventory database and a file associated with the end user of the article with the identification features of the retrieved article, and generating a purchase order for replacing the article that has been retrieved from the closet;

upon a request, by the user through the user interface of the closet, for replenishing of the closet, activating a scan of all articles already within the closet, locating any expired article, controlling unlocking of the door, and:

i) in case an expired article is detected, prompting the user to withdraw the detected expired article and, only when the detected expired article is withdrawn from the closet as detected by the presence sensor of the location of the detected expired article sending an absence signal, controlling a signaling unit into pointing out to a specific location within the closet in which a new incoming article is to be placed, the presence sensor of the specific location returning a presence signal once the new incoming article is placed in the specific location;

ii) in absence of a detected expired article, controlling a signaling unit into pointing out to a specific location within the closet in which a new incoming article is to be placed, the presence sensor of the specific location returning a presence signal once the new incoming article is placed in the specific location; and transferring, for each location within the closet, the response signal from the presence sensor together with the identification features of the associated article, to the inventory of the closet, thereby individually and independently continuously tracking each article from a supply thereof with the identification features thereof to a use thereof in relation to the end user in absence of intermediate identification input.

* * * * *